United States Patent [19]

Heppke et al.

[11] Patent Number: 4,855,429

[45] Date of Patent: Aug. 8, 1989

[54] CHIRAL ESTERS FORMED FROM α-SUBSTITUTED CARBOXYLIC ACIDS AND MESOGENIC HYDROXYL COMPOUNDS, AND THEIR USE AS DOPANTS IN LIQUID-CRYSTALLINE PHASES

[75] Inventors: Gerd Heppke; Christian Bahr, both of Berlin; Ingrid Müller, Hofheim am Taunus; Dieter Ohlendorf, Liederbach; Rainer Wingen, Hattersheim am Main, all of Fed. Rep. of Germany

[73] Assignee: Hoechst Aktiengesellschaft, Frankfurt am Main, Fed. Rep. of Germany

[21] Appl. No.: 55,246

[22] Filed: May 28, 1987

[30] Foreign Application Priority Data

May 30, 1986 [DE] Fed. Rep. of Germany ....... 3618213
Sep. 11, 1986 [DE] Fed. Rep. of Germany ....... 3630933
Feb. 4, 1987 [DE] Fed. Rep. of Germany ....... 3703228

[51] Int. Cl.$^4$ ............................................. C07D 239/02
[52] U.S. Cl. .................................... 544/335; 560/228; 560/109; 350/350 S; 350/346; 350/351; 544/318
[58] Field of Search ................ 544/335, 318; 560/228, 560/109; 350/350, 346, 351

[56] References Cited

PUBLICATIONS

CA106(2): 11301g (Pct. Int. Appl. WO86/87A1 Jan. 3, 1986).
CA84(13): 90108c (Z. Chem. 15(11) 441-3, 1975).
CA88(10): 67885c (Neth. Appl. NL 76/10144, Mar. 22, 1977).
CA88(24): 180588w (Med. Crystl. Lig. Cryst 42(1-3), 1225-41, 1977).

Primary Examiner—Paul J. Killos
Attorney, Agent, or Firm—Curtis, Morris & Safford

[57] ABSTRACT

The novel compounds are chiral esters formed from α-substituted carboxylic acids and mesogenic hydroxyl compounds of the general formula (I)

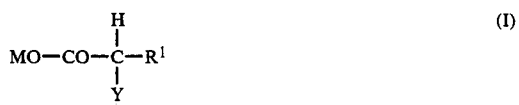

in which the symbols have the following meaning:
MO=molecular radical of a mesoganic hydroxyl compound MOH after removing an H, the radial MO being expressed by the general formula (II):

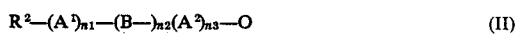

where the meaning of $R^2$ is a straight-chain or branched ($C_1$-$C_{12}$)alkyl or alkenyl, it being possible for one or two nonadjacent $CH_2$ groups to be replaced by O and/or S atoms, or if n1=1, also F, Cl, Br or CN, $A^1$, $A^2$ are, independently of each other, 1,4-phenylene, pyrimidine-2,5-diyl, 1,4-cyclohexylene, 1,3-dioxane-2,5-diyl, 1,3-dithiane-2,5-diyl, or 1,4-bicyclo(2,2,2)octylene, it being possible for said groups to be substituted at least singly by F, Cl, Br, CN and/or ($C_1$-$C_{12}$)alkyl (optionally, one or two nonadjacent $CH_2$ groups are replaced by O and/or S atoms), B is CO—O, O—CO, $CH_2$—$CH_2$, $OCH_2$, $CH_2O$, CH=N, N=CH, N=N N(O)=N, n1, n2, n3 are, independently of each other, 0, 1 or 2, n1 and n3 not being simultaneously 0, Y is F, Cl, Br, CN or $CF_3$, and $R^1$ is branched, ($C_3$-$C_9$)alkyl, benzyl or phenyl, the compounds having $R^1$=branched ($C_3$-$C_7$)alkyl, benzyl or phenyl, Y=F, Cl or Br, $R^2$=($C_1$-$C_{11}$)alkoxy, $A^1$, $A^2$=n1, n3=1 and n2=0 being excluded.

The compounds preferably find application in tilted smectic liquid-crystalline phases which they transform into ferroelectric liquid-crystalline phases; they have high values of spontaneous polarization.

7 Claims, No Drawings

CHIRAL ESTERS FORMED FROM α-SUBSTITUTED CARBOXYLIC ACIDS AND MESOGENIC HYDROXYL COMPOUNDS, AND THEIR USE AS DOPANTS IN LIQUID-CRYSTALLINE PHASES

DESCRIPTION

The characteristic curves of the electrooptical effects used in liquid-crystalline displays in general alter with temperature. In particular, with a multiplex-mode drive system this results in difficulties which may result in an undesirable restriction of the operating temperature range. In the case of various electrooptical effects, the addition of chiral compounds to the nematic liquid crystal can advantageously affect the temperature dependence of the electrooptical characteristic curve through the variation with temperature of the pitch of the cholesteric helical structure thereby induced, as in the case of the cholesteric-nematic phase transformation effect, the TN ("twisted nematic") cell and the recently announced SBE ("super-twisted birefringence effect").

In addition to the nematic and cholesteric liquid crystals, inclined ("tilted") smectic liquid-crystalline phases have been gaining in importance for some years, to an increasing extent, also for practical applications. If suitable dopants are added to such tilted smectic phases, in particular smectic C ($S_C$ or SmC) phases, which dopants exhibit a so-called spontaneous polarization ($P_s$), the phases mentioned can be transformed into a ferroelectric liquid-crystalline phase ($P_s$ specified in nC·cm$^{-2}$) (in this connection see, for example, Lagerwall et al. in the paper entitled "Ferroelectric Liquid Crystals for Displays", SID Symposium, October Meeting, 1985, San Diego (USA)).

In EP-A No. 0,159,872 compounds of the general formula below are described which are said to be suitable as components in liquid-crystalline systems:

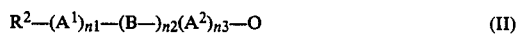

The substituents shall have the following meanings:
$R_a=(C_1-C_{18})$alkyl, X=F, Cl or Br and $R_b=$branched ($C_3-C_7$)alkyl, benzyl or phenyl. A value is specified for the spontaneous polarization of the compound having $R_a=C_8H_{17}$, X=Cl and $R_b=$1-methylpropyl of 210 nC·cm$^{-2}$.

The object of the present invention is to indicate compounds which, while having high values of spontaneous polarization $P_s$, have structural elements which also make them "compatible" (i.e. miscible) with other components in liquid-crystalline systems since, inter alia, the mesogenic part of the molecule is often responsible for good "compatibility" with other mixture components in liquid-crystalline systems.

The invention is based on the known chiral esters formed from α-substituted carboxylic acids and mesogenic hydroxyl compounds of the general formula (I)

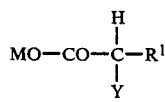

in which the symbols have the following meaning:
MO=molecular radical of a mesogenic hydroxyl compound MOH after removing an H, the radical MO being expressed by the general formula (II):

$$R^2-(A^1)_{n1}-(B-)_{n2}(A^2)_{n3}-O \qquad (II)$$

where the meaning of
$R^2$ is a straight-chain or branched ($C_1-C_{12}$)alkyl or alkenyl, it being possible for one or two nonadjacent $CH_2$ groups to be replaced by O and/or S atoms, or if n1=1, also F, Cl, Br or CN, $A^1$, $A^2$ are, independently of each other, 1,4-phenylene, pyrimidine-2,5-diyl, 1,4-cyclohexylene, 1,3-dioxane-2,5-diyl, 1,3-dithiane-2,5-diyl or 1,4-bicyclo(2,2,2)octylene, it being possible for said groups to be substituted at least singly by F, Cl, Br, CN and/or ($C_1-C_{12}$)alkyl (optionally, one or two nonadjacent $CH_2$ groups are replaced by O and/or S atoms), B is CO—O, O—CO, $CH_2-CH_2$, $OCH_2$, $CH_2O$, CH=N, N=CH, N=N N(O)=N, n1, n2, n3 are, independently of each other, 0, 1 or 2, n1 and n3 not being simultaneously 0, Y is F, Cl, Br, CN or $CF_3$, and $R^1$ is branched ($C_3-C_9$)alkyl, benzyl or phenyl, the compounds having $R^1=$branched ($C_3-C_7$)alkyl, benzyl or phenyl, Y=F, Cl or Br, $R^2=(C_1-C_{11})$alkoxy, $A^1$, $A^2=$phenyl, n1, n3=1 and n2=0 being excluded.

The compounds mentioned are chiral α-substituted (i.e. substituted in the 2 position of a chiral branched alkanoic acid) alkanoic acid esters of phenols (or comparable heterocyclic compounds) or cycloalkanols.

A further embodiment of the invention is a twistable liquid-crystal phase with a content of at least one chiral compound which contains at least one compound of the general formula (I) as the chiral compound. The term "twistable liquid-crystalline phase" is understood to mean nematic, cholesteric or inclined ("tilted") smectic phases, in particular SmC phases.

The twisted liquid-crystalline phases consist of 2 to 20, preferably 2 to 15 components, including at least one of the chiral compounds claimed by the invention. The other constituents are preferably selected from the known compounds having nematic, cholesteric and/or tilted smectic phases, which include, for example, Schiff's bases, biphenyls, terphenyls, phenylcyclohexanes, cyclohexylbiphenyls, pyrimidines, cinnamic acid esters, cholesterol esters, variously bridged, terminally polar polynuclear esters of p-alkylbenzoic acids. In general, even before the addition of the chiral compound(s), liquid-crystalline phases obtainable commercially already exist as mixture of a wide range of components, at least one of which is mesogenic, i.e. exhibits a liquid-crystalline phase in the form of a derivative or in a mixture with certain cocomponents [=the formation of at least an enantiotropic (clearing point>melting point) or monotropic (clearing point<melting point) phase may be expected].

In particular, the twistable liquid-crystalline phase contains, in addition to at least one of the chiral compounds claimed by the invention, a phenylpyrimidine compound having $S_c$ phase, e.g. a 4-(5-alkylpyrimidin-2-yl)-1-alkoxybenzene, or an ester compound having $S_c$ phase, e.g. a phenyl 4-alkyloxybenzoate.

Of the compounds of the general formula (I), those are preferred in which the symbols have the following meaning: $R^2$ = straight-chain or branched ($C_4$-$C_{10}$)alkyl or alkenyl, it being possible for a $CH_2$ group to be replaced by an O or S atom, $A^1$, $A^2$ = independently of each other, unsubstituted, 1,4-phenylene, 1,4-cyclohexylene or pyrimidine-2,5-diyl, B=CO—O, O—CO, $CH_2O$, or CH=N, n1=1 or 2, n2=0 or 1 and n3=1 or 2, Y=Cl or $CF_3$, and $R^1$ = branched ($C_3$-$C_6$)alkyl. Particularly preferred are compounds of the general formula (I) having two chiral centers in the radical deriving from the carboxylic acid, i.e. having one chiral center on the α-C atom and a further chiral center on the $R^1$ radical.

The liquid-crystalline phase in general contain 0.01 to 70% by weight, in particular 0.05 to 50% by weight, of the novel compound(s).

The compounds according to the invention can be prepared by reaction of mesogenic compounds of the formulas (III) or (III')

MOH     (III)

$(MO)_mMe$    (III')

in which M has the above meaning, Me stands for earth alkali metal or preferably alkali metal, and m=1 (alkali metal) or 2 (earth alkali metal), with compounds of the formula (IV)

$$XCO-\underset{\underset{Y}{|}}{\overset{\overset{H}{|}}{C}}-R^1 \quad (IV)$$

in which X is OH or halogen, preferably chlorine, and Y and $R^1$ have the meanings above.

For this process hydroxyl compounds (III) and acid chlorids (IV) (X=Cl) are preferably used, and the reaction is carried through in the presence of acid acceptors, like amines, for example pyridine or triethyl amine, or alkali or earth alkali (hydrogen) carbonates, normaly at temperatures of −40° to +20° C. The purification of the raw product so obtained can be done in the usual way, for example by column chromatography and/or by recrystallization.

The novel compounds are suitable in particular as dopants for tilted smectic liquid-crystalline phases since they convert them into ferroelectric liquid-crystalline phases; the values of the spontaneous polarization ($P_s$) are in the range from 30 to 250 nC·cm$^{-2}$ (linearly extrapolated to the pure compound).

EXAMPLES

Preparation of the α-halocarboxylic acid (Y=Cl)

0.2 mol of (S)-α-amino acid is dissolved in 250 ml of 6N HCl at room temperature. 0.3 mol of $NaNO_2$ is added to the latter in small batches while stirring so that the temperature remains below 30° C. After addition is complete, stirring is continued for a further 4 h at room temperature. Extraction is carried out 3 times with ether, the ether phase is dried over $MgSO_4$ and the ether distilled off. The yield of (S)-α-chlorocarboxylic acid is 0.14 to 0.16 mol. The other α-substituted carboxylic acids having Y=F or Br can also be synthesized correspondingly. The preparation of the corresponding cyano or trifluoromethyl compounds is known from the literature and reference is made to standard works.

Preparation of the acid chloride 60 ml of $SOCl_2$ are added to 0.2 mol of (S)-α-substituted carboxylic acid. The reaction mixture is stirred for 3 h at 50° C. and the excess $SOCl_2$ is then distilled off. The residue is distilled in vacuo, after which about 0.10 to 0.18 mol of the (S)-α-substituted carboxylic acid chloride is obtained.

General instruction for the preparation of the compounds (I)

0.01 mol of the hydroxyl compound MOH is dissolved in 50 ml of pyridine and 0.01 mol of the acid chloride described above is added to the latter. The reaction mixture is stirred for 1 h at room temperature. The pyridinehydrochoride precipitated is filtered off and the pyridine is distilled off. The residue is purified by column chromatography (silica gel deactivated with 6% by weight of $H_2O$, solvent: methylene chloride) and the product recrystallized three to five times from ethanol; the yield is 20 to 60%.

EXAMPLES 1 TO 6

I, MO = $R^2-(A^1)_1-(B)_o-(A^2)_1-O$ with

The mesogenic hydroxyl compound is known from the literature (e.g. DE-C No. 2,257,588).

TABLE 1

| Ex. No. | $R^2$ | $R^1$ | Phase sequence (°C.) |
|---|---|---|---|
| 1 | $H_{19}C_9$ | —CH(CH$_3$)$_2$ | K 46 I |
|   |   |   | ($S_C$30 $S_A$36 I) |
| 3 | $H_{15}C_7$ | —CH$_2$CH(CH$_3$)$_2$ | K 57 I |
| 4 | $H_{17}C_8$ | " | K 32 I |
| 5 | $H_{15}C_7$ | (S)—CH(CH$_3$)C$_2$H$_5$ | K 58 I |
| 6 | $H_{17}C_8$ | " | K 45 I |

Key: (K = crystalline, I = isotropic, $S_A$, $S_B$, $S_C$, $S_I$ = smectic A, B, C or I phases; Values in brackets: phase sequence on cooling EXAMPLES 7 to 14

I, MO = $R^2-(A^1)_1-(B)_0-(A^2)_1-O-$ with

The mesogenic hydoxyl compound is known from the literature (eg. Heterocycles, Vol. 19, No. 6, 1079–1082 (1982)).

TABLE 2

| Ex. No. | $R^2$ | $R^1$ | Phase sequence (°C.) |
|---|---|---|---|
| 10 | $H_{17}C_8$ | —CH$_2$CH(CH$_3$)$_2$ | K 28 I |
|    |   |   | (K 19 $S_A$22 I) |
| 11 | $H_{23}C_{11}$ | " | K 49 I |
| 12 | $H_{17}C_8$ | (S)—CH(CH$_3$)C$_2$H$_5$ | K 50 I |
| 13 | $H_{19}C_9$ | " | K 52 I |
|    |   |   | (K 10 $S_A$26 I) |
| 14 | $H_{23}C_{11}$ | " | K 56 I |
|    |   |   | (K? $S_B$21 $S_A$29 I) |

EXAMPLES 15 TO 17

I, MO = $R^2-(A^1)_1-(B)_0-(A^2)_1-O-$ with

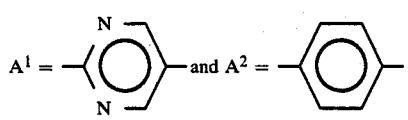

The mesogenic hydroxyl compound is known from the literature (e.g. H. Zaschke, Diss. B, Univ. of Halle, 1977).

TABLE 3

| Ex. No. | $R^2$ | $R^1$ | Phase sequence (°C.) |
|---|---|---|---|
| 15 | $H_5C_2O-$ | (S)—$CH(CH_3)C_2H_5$ | K 97 I |
| 16 | $H_{17}C_8O-$ | " | K 66 I |
| 17 | $H_{19}C_9O-$ | " | K 69 I |
| | | | (K 35 $S_A$49 I) |

EXAMPLES 18 TO 23

I, MO = $R^2-(A^1)_1-(B)_0-(A^2)_1-O-$ with

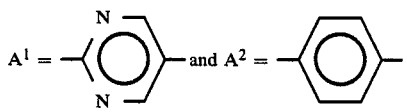

The mesogenic hydroxyl compound is known from the literature (e.g. H. Zaschke, et al., Z. Chem. 1], 293 (1977)).

TABLE 4

| Ex. No. | $R^2$ | $R^1$ | Phase sequence (°C.) |
|---|---|---|---|
| 17 | $H_{15}C_7S-$ | (S)—$CH(CH_3)C_2H_5$ | K 73 I |
| 20 | $H_{17}C_8S-$ | " | K 65 I |
| 21 | $H_{19}C_9S-$ | " | K 67 I |
| 22 | $H_{21}C_{10}S-$ | " | K 63 I |
| 23 | $H_{23}C_{11}S-$ | " | K 71 I |

EXAMPLES 24 TO 27

TABLE 10

| Compound Ex. No. | Proportion of compound in mol % | $S_c^*$ range of the mixture in °C. | $P_s$ | $\tau$ | $2\theta$ |
|---|---|---|---|---|---|
| 10 | 10 | 22 to 46 (10) | 7.5 | 150 | 45 |
| 10 | 25 | 34 to 39 (15) | 19 | 17 | 37 |
| 12 | 10 | 15 to 46 (0) | 13 | 48 | 42 |
| 12 | 25 | 27 to 42 (16) | 38 | 20 | 47 |
| 13 | 10 | 6 to 49 (0) | 14 | 48 | 48 |
| 13 | 17.5 | 13 to 45 (2) | 25 | 20 | 49 |
| 13 | 25 | 21 to 42 (6) | 32 | 12 | 50 |
| 14 | 10 | 16 to 49 (3) | 14 | 38 | 44 |
| 14 | 17.5 | 23 to 47 (6) | 23 | 35 | 50 |
| 14 | 25 | 38 to 46 (10) | 36 | 30 | 50 |

I, MO = $R^2-(A^1)_1-(B)_0-(A^2)_1-O-$ with

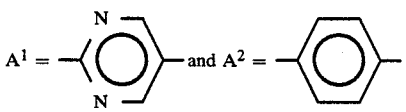

If corresponding starting materials are used, the mesogenic hydroxyl compounds are obtained as in Examples 15 to 17 or 18 to 23.

TABLE 5

| Ex. No. | $R^2$ | $R^1$ | Phase sequence (°C.) |
|---|---|---|---|
| 24 | (S)—$H_5C_2CH(CH_3)CH_2O-$ | (S)—$CH(CH_3)C_2H_5$ | K 83 I |
| 25 | (S)—$(H_3C)_2C=CHCH_2CH(CH_3)CH_2CH_2O-$ | " | K 44 I |
| 26 | $H_2C=CH-(CH_2)_9O-$ | " | K 74 I |
| 27 | (S)—$H_5C_2CH(CH_3)(CH_2)_5S-$ | " | K 82 I |

EXAMPLE 28

I, MO = $R^2-(A^1)_1-(B)_1-(A^2)_1-O-$ with

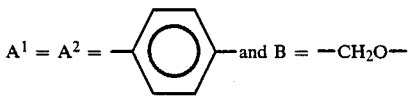, B = $-\underset{\underset{O}{\|}}{C}-O-$, $R^2 = H_{15}C_7O-$ and $R^1 = -CH(CH_3)_2$ are obtained by reacting 4-benzyloxyphenol with the above-mentioned acid chloride in accordance with the instruction also specified above, hydrogenation of this reaction product and reaction of the phenolic compound obtained with 4-heptyloxybenzoyl chloride.

EXAMPLES 29 TO 33

I, MO = $R^2-(A^1)_1-(B)_1-(A^2)_1-O-$ with $A^1 = A^2 = $ 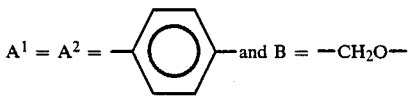 and B = $-CH_2O-$ are obtained by reaction of 4-benzyloxyphenol with the acid chloride mentioned above according to the instruction already mentioned, hydrogenation of this reaction product and reaction of the phenolic compound obtained with 4-$R^2$-benzyl alcohol by the method which has been described by O. Mitsunobu, Synthesis 1987, 1.

TABLE 6

| Ex. No. | $R^2$ | $R^1$ | Phase sequence (°C.) |
|---|---|---|---|
| 29 | $H_{17}C_8O-$ | $(S-)-CH(CH_3)C_2H_5$ | K 59 I |
| 30 | $(S)-H_5C_2CH(CH_3)(CH_2)_5O-$ | " | K 50 I (K8 $S_A$24 I) |
| 31 | $H_{21}C_{10}O-$ | " | K 58 I (K29 $S_A$37 I) |
| 32 | " | $-CH_2CH(CH_3)_2$ | K 57 I |

EXAMPLES 34 AND 35

I, MO = $R^2-(A^1)_2-(B)_1-(A^2)_1-O-$ with $A^1 = $ –⟨O⟩– , $A^2 = $ –⟨O⟩– and B = $-CH_2O-$ are obtained analogously to Examples 29 to 33.

TABLE 7

| Ex. No. | $R^2$ | $R^1$ | Phase sequence (°C.) |
|---|---|---|---|
| 34 | $H_{17}C_8-$ | $(S)-CH(CH_3)C_2H_5$ | K78 $S_j$95 $S_C$118 $S_A$130 I |
| 35 | " | $-CH_2CH(CH_3)_2$ | $S_X$50 $S_I$104 $S_C$118 $S_A$130 I |

EXAMPLES 36 AND 37

I, MO = $R^2-(A^1)_1-(B)_1-(A^2)_1-O-$ with $A^1 = A^2 = $ –⟨O⟩– and B = $-CH=N-$ are obtained by condensation of 4-$R^2$-benzaldehyde with 4-aminophenol and subsequent esterification of this azomethine with the abovementioned acid chloride.

TABLE 8

| Ex. No. | $R^2$ | $R^1$ | Phase sequence (°C.) |
|---|---|---|---|
| 36 | $H_{21}C_{10}O-$ | $(S)-CH(CH_3)C_2H_5$ | K60 $S_A$73 I (K39 $S_C$58 $S_A$73 I) |
| 37 | " | $-CH_2CH(CH_3)_2$ | K62 $S_A$68 I (K54 $S_C$54 $S_A$68 I) |

Application examples

To check the effectiveness of the compounds described above as dopants in liquid-crystalline systems, they are each mixed in concentrations of 10 mol-% (or in individual cases of 17.5 and 25 mol-%) with the racemate of the compound $\text{WWW}-⟨N\text{pyrimidine}N⟩-⟨O⟩-O-\text{WWV}$  A Phase sequence: K 14.9° C. $S_c$ 49.8° C. $S_A$ 59.2° C. I (5° C.)

4-(5-octylpyrimidin-2-yl)-1-(6-methyloctyl-1-oxy)-benzene or the compound $\text{WWW}-O-⟨O⟩-\overset{O}{\underset{\|}{C}}-O-⟨O⟩-O-\text{WW}$  B Phase sequence: K 17° C. $S_G$ 32.7° C. $S_C$ 70.4° C. $S_A$ 73.3° C. I (−3° C.)

4-(4-decyloxyphenyl-1-carbonyloxy)-1-(4-methylhexyloxy)benzene and the values of the spontaneous polarization ($P_s$ in nC·cm$^{-2}$), the switching time $\tau$ (in μs) and the optical tilt angle of the $S_c$ phase $\theta$ (in °) of the mixture are determined. The $P_s$ values are measured by the method of H. Diamant et al. (Rev. Sci. Instr., 28, 30, 1957), a special measuring cell [Skarp et al., in Ferroelectric Letters, Vol. 06, 000 (1986)] in which the $\tau$ and $\theta$ values are also determined. With a cell path length of approx. 2 μm, a uniform planar orientation of the liquid crystal in the $S_c$ phase is achieved by shearing action [SSFLC Technique, Clark et al., Appl. Phys. Lett. 36, 899 (1980)]. To determine $\tau$ and $\theta$, the measuring cell is mounted on the revolving stag of a polarization microscope between crossed analyzer and polarizer. The optical tilt angle or switch angle, 2$\theta$, is determined by rotating the measuring cell from maximum to minimum light transmission. A photodiode is used to determine the switching time, $\tau$, the rise time of the light signal from 10 to 90% signal amplitude being measured. The tables summarize the results for the mixtures. In addition to the values of $P_s$, $\tau$ and 2$\theta$, the $S_c$ range of the mixture concerned is specified; here the values in brackets specify the lower temperature limit of the $S_c$ range achievable by supercooling.

With the compound A (B) being used as host for receiving the dopant, all the values for $P_s$, $\tau$ and 2$\theta$ are referred to a temperature of 25° C. (40° C.).

Table 9 summarizes some results for the chiral compounds of the type $C_nH_{2n+1}-⟨N\text{pyrimidine}N⟩-⟨O⟩-O-CO-\overset{*}{C}H-R^1$
                                            |
                                            Cl which were investigated exclusively as dopants in the compound A.

TABLE 9

| Compound Ex. No. | Proportion of compound in mol % | $S_c$* range of the mixture in °C. | $P_s$ | $\tau$ | 2$\theta$ |
|---|---|---|---|---|---|
| 4 | 10 | 10 to 28 (3) | 0.2 | 15 | 8 |
| 5 | 10 | 10 to 33 (0) | 3.5 | 55 | 21 |
| 6 | 10 | 7 to 37 (3) | 6.5 | 27 | 27 |

Table 10 contains results for the compounds

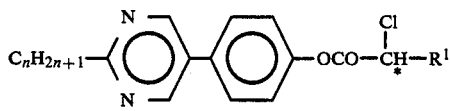

when used as dopants in the compound A. As a comparison of Tables 9 and 10 and in particular, the comparison of compounds 4 and 10, and also of 6 and 12 shows, the reversal of the pyrimidine group improves the mixture behavior of the compounds mentioned i.e. the $S_c$ range of the host compound A is less restricted by adding compounds 10 and 12 than by 4 and 6.

TABLE 10

| Compound Ex. No. | Proportion of compound in mol % | $S_c^*$ range of the mixture in °C. | $P_s$ | $\tau$ | $2\theta$ |
|---|---|---|---|---|---|
| 10 | 10 | 22 to 46 (10) | 7.5 | 150 | 45 |
| 10 | 25 | 34 to 39 (15) | 19 | 17 | 37 |
| 12 | 10 | 15 to 46 (0) | 13 | 48 | 42 |
| 12 | 25 | 27 to 42 (16) | 38 | 20 | 47 |
| 13 | 10 | 6 to 49 (0) | 14 | 48 | 48 |
| 13 | 17.5 | 13 to 45 (2) | 25 | 20 | 49 |
| 13 | 25 | 21 to 42 (6) | 32 | 12 | 50 |
| 14 | 10 | 16 to 49 (3) | 14 | 38 | 44 |
| 14 | 17.5 | 23 to 47 (6) | 23 | 35 | 50 |
| 14 | 25 | 38 to 46 (10) | 36 | 30 | 50 |

Table 11 summarizes some results for mixtures of the chiral compounds

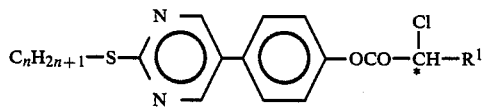

with the compound A. As a comparison of Tables 10, 11 and 12 and in particular, of compounds 6, 12 and 20, and also 14 and 23 shows, the mixture behavior of the dopants mentioned is again improved by the introduction of the thioether bridge. Surprisingly, even the compounds 20 and 27 increase the $S_c$ range of the host compound A if 10 mol-% are added. This property is of considerable advantage for the practical application of the dopants mentioned in which as large $S_c$ ranges as possible are required.

TABLE 11

| Compound Ex. No. | Proportion of compound in mol % | Host | $S_c^*$ range of the mixture in °C. | $P_s$ | $\tau$ | $2\theta$ |
|---|---|---|---|---|---|---|
| 18 | 10 | A | 15 (1) to 46 | 10.7 | 37 | 48.5 |
| 20 | 10 | A | 6.7 (1) to 49.5 | not investigated | | |
| 23 | 10 | A | 18.7 (1) to 49.5 | 12.5 | 30 | 48 |
| 23 | 25 | A | 29.4 (15) to 41 | 35 | 20 | 52 |
| 27 | 10 | A | 0 (0) to 47 | 14 | 48 | 51 |

Table 12 summarizes some results for mixtures of the chiral compounds

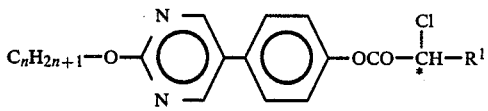

with compound A and compound B. The comparison of Tables 10, 11 and 13 and in particular, of compounds 6, 12 and 16, and also 13 and 17 shows that the introduction of the ether bridge also improves the mixture behavior of the dopants mentioned. Surprisingly, doping compounds A and B with 10 mol-% of the compounds 16 and 17 leads even to an increase in the $S_c$ range of the two compounds A and B.

TABLE 12

| Compound Ex. No. | Proportion of compound in mol % | Host | $S_c^*$ range of the mixture in °C. | $P_s$ | $\tau$ | $2\theta$ |
|---|---|---|---|---|---|---|
| 16 | 10 | A | 3.7 (0) to 49.5 | 14 | 40 | 51 |
| 16 | 25 | A | 17.3 (−5) to 49.5 | 38.5 | 25 | 57 |
| 17 | 10 | A | 4.0 (0) to 52 | 13 | 60 | 48 |
| 17 | 10 | B | 20.6 (20) to 62.8 | 7 | 70 | 53 |
| 25 | 10 | A | 10.4 (0) to 38 | 13 | 55 | 51 |
| 26 | 10 | A | 4.2 (−2) to 38 | 13 | 62 | 50 |

Table 13 summarizes some results for mixtures of the chiral compounds

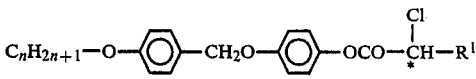

with the host compounds A and B. As can be seen from Table 13, the dopants mentioned exhibit a very good mixture behavior both in host compounds of type A and also B, i.e. the width of the $S_c$ phase of the host compounds is only slightly affected or even increased with 10 mol-% doping.

TABLE 13

| Compound Ex. No. | Proportion of compound in mol % | Host | $S_c^*$ range of the mixture in °C. | $P_s$ | $\tau$ | $2\theta$ |
|---|---|---|---|---|---|---|
| 29 | 10 | A | 10 (5) to 48 | 9.6 | 78 | 42 |
| 31 | 10 | A | 10.4 (5) to 48 | 4.4 | 42 | 40 |
| 31 | 10 | B | 27.7 (27.1) to 65 | 10 | 45 | 57 |
| 31 | 17.5 | B | 23.5 (23.2) to 60.5 | 20.2 | 36 | 58 |
| 32 | 10 | B | 29.6 (29) to 64 | 7 | 50 | 57 |
| 30 | 10 | A | 10 (0) to 48.2 | 13.2 | 50 | 46 |

Table 14 summarizes some results for mixtures of the chiral compounds

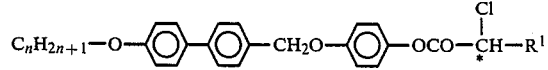

with the host compounds A and B. Surprisingly, the two compounds 34 and 35 are themselves liquid-crystalline and exhibit an $S_c$ phase. They exhibit a very good mixture behavior in the host compounds A and B and, as is evident from Table 14, increase the $S_c$ ranges of the host compounds if 25 mol-% are added.

TABLE 14

| Compound Ex. No. | Proportion of compound in mol % | Host | $S_c$* range of the mixture in °C. | $P_s$ | $\tau$ | $2\theta$ |
|---|---|---|---|---|---|---|
| 35 | 25 | B | 37 (35) to 72.5 | 22 | 25 | 58 |
| 34 | 25 | A | 7.3 (−4) to 62 | 32 | 37 | 41 |
| 34 | 25 | B | 30 (29.2) to 74 | not investigated | | |
| 35 | 100 | — | pure compound 103.6 to 117.6 | 105 | 25 | 44* |
| 34 | 100 | — | pure compound 95 to 118 | 80 | 33 | 54* |

*$P_s$, $\tau$, $2\theta$ - values in each case for the pure compounds at 105°C.

The compound (Ex. 36)

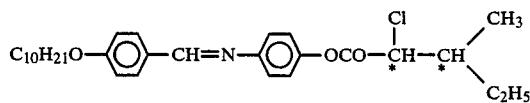

increases the $S_c$ range of the host compound B to 26.6 (28) °C. to 68° C. for 10 mol-% doping. The measurements at 40° C. are: $P_s$=7.9 nC/cm², $\tau$=20 μs and $2\theta$=47°

We claim:

1. A chiral ester of the formula (I)

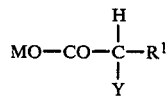

wherein MO is a molecular radical of a mesogenic hydroxyl compound MOH after removing an H, the radical MO having the formula (II)

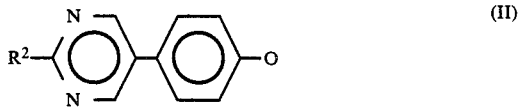

wherein $R^2$ is straight-chain or branched ($C_1$-$C_{12}$)alkyl or alkenyl, where one or two non-adjacent CH$_2$ groups may be replaced by O or S, or wherein $R^2$ is F, Cl, Br or CN;

Y is F, Cl, Br, CN or CF$_3$; and $R^1$ is a branched ($C_3$-$C_9$)alkyl, benzyl or phenyl.

2. A chiral ester as claimed in claim 1, wherein $R^2$ is a straight-chain or branched ($C_4$-$C_{10}$)alkyl or alkenyl, where one CH$_2$ group may be replaced by O or S; Y is Cl or CF$_3$; and $R^1$ is a branched ($C_3$-$C_6$)alkyl.

3. A chiral ester as claimed in claim 1, wherein the radical $R^1$ in the formula (I) has a further chiral center.

4. A twistable liquid-crystalline mixture which comprises at least one chiral compound of the formula (I) as claimed in claim 1.

5. A liquid-crystalline display element containing a liquid-crystalline mixture as claimed in claim 4.

6. A method for converting a tilted smectic liquid-crystalline mixture into a ferroelectric liquid-crystalline mixture, which comprises adding at least one compound of the formula (I) as claimed in claim 1 to the liquid-crystalline mixture.

7. A chiral ester as claimed in claim 1, which is (S)-4-(2-octylpyrimidine-5-yl)phenyl 2-chloro-4-methylpentanoate; (S)-4-(2-undecylpyrimidine-5-yl)phenyl 2-chloro-4-methylpentanoate; (S)-4-(2-octylpyrimidine-5-yl)phenyl 2-chloro-3-methylpentanoate; (S)-4-(2-nonylpyrimidine-5-yl)phenyl 2-chloro-3-methylpentanoate; (S)-4-(2-undecylpyrimidine-5-yl)phenyl 2-chloro-3-methylpentanoate; (S)-4-(2-ethyloxypyrimidine-5-yl)phenyl 2-chloro-3-methylpentanoate; (S)-4-(2-octyloxypyrimidine-5-yl)phenyl2-chloro-3-methylpentanoate; (S)-4-(2-nonyloxypyrimidine-5-yl)phenyl 2-chloro-3-methylpentanoate; (S)-4-(2-heptylthiopyrimidine-5-yl)phenyl 2-chloro-3-methylpentanoate; (S)-4-(2-octylthiopyrimidine-5-yl)phenyl 2-chloro-3-methylpentanoate; (S)-4-(2-nonylthiopyrimidine-5-yl)phenyl 2-chloro-3-methylpentanoate; (S)-4-(2-decylthiopyrimidine-5-yl)phenyl 2-chloro-3-methylpentanoate; (S)-4-(2-undecylthiopyrimidine-5-yl)phenyl 2-chloro-3-methylpentanoate; (S)-4-[2-((S)-2-methylbutyl)oxypyrimidine-5yl]phenyl 2-chloro-3-methylpentanoate; (S)-4-[2-((S)-3,6-methyl-5-heptenyl)oxypyrimidine-5-yl]-phenyl 2-chloro-3-methylpentanoate; (S)-4-[2-(9-undecenyl)oxypyrimidine-5-yl]phenyl 2-chloro-3-methylpentanoate; and (S)-4-[2-((S)-6-methyloctyl)oxypyrimidine-5-]phenyl 2-chloro-3-methylpentanoate.

* * * * *